US006733572B2

(12) United States Patent
Reyes et al.

(10) Patent No.: US 6,733,572 B2
(45) Date of Patent: May 11, 2004

(54) SEPARATION OF PROPYLENE AND DIMETHYLETHER FROM HYDROCARBON MIXTURES

(75) Inventors: Sebastian C. Reyes, Branchburg, NJ (US); Krishnan V. Venkatesan, Mt. Laurel, NJ (US); Gregory J. DeMartin, Flemington, NJ (US); John H. Sinfelt, Oldwick, NJ (US); Karl G. Strohmaier, Port Murray, NJ (US); Jose Guadalupe Santiesteban, Bethlehem, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 22 days.

(21) Appl. No.: 10/210,566

(22) Filed: Jul. 30, 2002

(65) Prior Publication Data

US 2004/0020360 A1 Feb. 5, 2004

(51) Int. Cl.$^7$ ............................................... B01D 53/02
(52) U.S. Cl. ............................. 95/96; 95/143; 95/144; 95/902; 95/115; 585/824
(58) Field of Search ..................... 95/90, 96–103, 95/115, 143, 144, 148, 900, 902; 423/328.2, DIG. 30; 208/310; 585/809, 820, 824, 825

(56) References Cited

U.S. PATENT DOCUMENTS

| | | | |
|---|---|---|---|
| 6,001,320 A | | 12/1999 | Addiego .................. 423/239.2 |
| 6,200,366 B1 | * | 3/2001 | Bulow et al. ................. 95/101 |
| 6,293,999 B1 | | 9/2001 | Cheng et al. .................. 95/96 |
| 6,296,688 B1 | | 10/2001 | Cheng et al. ................. 95/101 |
| 6,488,741 B2 | * | 12/2002 | Olson .......................... 95/144 |
| 2003/0004386 A1 | * | 1/2003 | Lattner et al. .............. 585/804 |
| 2003/0125597 A1 | * | 7/2003 | Cheng et al. ............... 585/639 |

FOREIGN PATENT DOCUMENTS

| | | |
|---|---|---|
| EP | 572 239 | 10/1996 |
| EP | 943 595 | 2/1999 |
| WO | WO 2003020671 A1 * | 3/2003 |

* cited by examiner

Primary Examiner—Frank M. Lawrence

(57) ABSTRACT

The present invention is a process for separating propylene and dimethylether from a mixture comprising propylene, dimethylether, and propane. The mixture is passed through a bed of an adsorbent comprising a porous crystalline material having (i) diffusion time constants for dimethylether and propylene of at least 0.1 sec$^{-1}$, and (ii) a diffusion time constant for propane of than 0.02 of the diffusion time constants for dimethylether and propylene. The bed preferentially adsorbs propylene and dimethylether from the mixture. The adsorbed propylene and dimethylether are then desorbed from the bed.

16 Claims, 5 Drawing Sheets

SEPARATION OF PROPYLENE AND DIMETHYLETHER FROM HYDROCARBON MIXTURES

CROSS REFERENCE TO OTHER RELATED APPLICATIONS

This application is related in subject matter to co-pending U.S. patent application Ser. No. 10/100,978.

FIELD

This invention relates to a process for separating propylene and dimethylether from mixtures of low molecular weight hydrocarbons.

BACKGROUND

The separation of low molecular weight hydrocarbons in mixed hydrocarbon streams is an extremely important and large volume operation in the chemical and petrochemical industries. Catalytic cracking and steam cracking are among the most common and large-scale processes leading to these mixed hydrocarbon streams. The chemical conversion of oxygenates to olefins, such as the conversion of methanol to olefins (MTO), is another potential source of these hydrocarbon streams that require purification before final use or to improve overall process economics via recycle.

The MTO process typically uses low acidity silicoaluminophosphate catalysts to drive the transformation of methanol to ethylene and propylene in high yields. Typical pilot plant data indicates that, excluding water by-product and unreacted methanol, the major components in the reactor effluent are ethylene (approximately 40 wt %), propylene (approximately 40 wt %), $C_4+$ (approximately 14 wt %), ethane (approximately 1 wt %), propane (approximately 1 wt %), and dimethylether (approximately 1 wt %). The process is accompanied by coke formation (approximately 3 wt %) and by lesser amounts of CO, $CO_2$, $CH_4$, ethers, ketones, acids, alcohols, and aldehydes. Even though the composition of the MTO product differs from that obtained in conventional steam crackers, the post-processing equipment required to produce polymer grade ethylene and propylene is largely the same. Ongoing process development studies indicate that one of the main differences lies in the $C_3$ splitter, which is the final step in the generation of a high purity propylene stream.

In steam cracking, the feed to the $C_3$ splitter contains primarily propylene and propane because prior to entering the splitter, this stream is selectively hydrogenated to transform residual methylacetylene and propadiene (MAPD) into additional propylene (and propane). In MTO, due to the milder reaction temperatures, the amount of MAPD is negligibly small but dimethylether is readily formed by dehydration of methanol. Paralleling the situation in steam cracking, efforts are underway to selectively react the dimethylether to prevent the potential contamination of the high purity propylene stream. However, recent vapor-liquid equilibrium calculations indicate that dimethylether will end up with propane in the bottoms of the $C_3$ splitter and thus no feed pretreatment will be necessary. Moreover, since the propylene recovery in the splitter is less than 100%, this bottoms stream will also contain propylene.

Under this scenario, the $C_3$ splitter bottoms stream will contain valuable dimethylether and propylene, but unless these are separated from the propane, the stream is currently expected to have fuel value only. However, if dimethylether could instead be recovered, recycled, and converted into olefin products, an additional 2 wt % ethylene equivalent could be produced. For a large-scale plant of 1000 kTa ethylene this would amount to about 54.8 T/day and could increase further if methanol conversion in the MTO reactor were to decrease by design or by other unit constraints. Similarly, the recoverable propylene represents an additional 2.17%, which amounts to 59.5 T/day for a 1000 kTa propylene plant.

The close proximity in boiling points between propylene and propane, in particular, suggests that conventional distillation may not provide an economically viable method of separating dimethylether and propylene from propane. An object of the present invention is therefore to provide an alternate process for selectively recovering dimethylether and propylene from a mixture containing propane.

Some of the leading alternatives to fractional cryogenic distillation involve the use of adsorbents that exploit their ability to adsorb some of the components selectively. This has given rise to various forms of pressure or temperature swing adsorption (PSA/TSA) processes in which the mixture is first passed through an adsorbent material under conditions where one or more of the components are selectively removed. The loaded material is then typically exposed to a lower pressure and/or higher temperature environment where the adsorbed components are released and recovered at a higher purity level. Economic viability requires adsorbent materials that can deliver high selectivity, high adsorption capacity, and short duration cycles. An additional and critically important requirement is that the material should not catalyze chemical reactions that might lower the recovery of the desired components and/or render the adsorbent inactive. This is a particularly demanding condition when dealing with olefins and oxygenates.

Among the adsorbents which have been proposed for the recovery of propylene from hydrocarbon mixtures are ion exchange resins, mesoporous solids, activated carbons, and zeolites. Ion exchange resins and mesoporous solids usually exploit equilibrium adsorption properties in which one of the components is selectively adsorbed over suitably dispersed chemical agents. They principally rely on the adsorption affinity of cationic active centers such as Ag and Cu ions for the double bond in propylene ($\pi$-complexation). The duration of the adsorption cycle is that required to bring the mixture close to thermodynamic equilibrium with the adsorbent. The relative rates of diffusion of the various components within the adsorbent are of secondary importance but the total time for equilibration is preferably kept low for economic reasons.

Unlike traditional equilibrium separations that rely on the preferential adsorption of some of the components, kinetic-based separation processes rely on the property of some of the components to diffuse more rapidly than others into the adsorbent material. Two related cases of diffusion control are of interest. In one extreme case, the separation is achieved by excluding the diffusion of some of the components into the adsorbent. The second case exploits a sufficiently large difference in diffusion rates to allow the preferential uptake of some of the components within a predetermined adsorption time.

Activated carbons and zeolite adsorbents typically resort to a combination of adsorption affinity and diffusion control. Thus, carbons are usually activated to very high surface area forms in order to provide textural properties and pore sizes that maximize adsorption while selectively controlling diffusion. Crystalline microporous materials have become even more attractive than activated carbons because of the ever increasing possibilities afforded by new synthetic routes, which allow for a more flexible and precise control of chemical composition, pore size, and pore volume. The tetrahedrally coordinated atoms in these microporous materials form ring structures of precise dimensions that selectively control the diffusional access to the internal pore volume.

8-membered ring zeolites, in particular, have been actively investigated for the separation of small molecular weight hydrocarbons because their, window sizes are very comparable to molecular dimensions and because they can provide high adsorption capacities. A typical example is the Linde type A zeolite, which is characterized by a set of three-dimensional interconnected channels having 8-membered ring window apertures. The effective size of the windows depends on the type of charge-balancing cations. This has given rise to the potassium (3A), sodium (4A), and calcium (5A) forms, which have nominal window sizes of about 3 Å, 3.8 Å, and 4.3 Å, respectively.

Thus, for example, EP-B-572239 discloses a PSA process for separating an alkene, such as propylene, from a mixture comprising said alkene and one or more alkanes by passing the mixture through at least one bed of zeolite 4A at a temperature above 323° K to preferentially adsorb said alkene and then desorbing the alkene from the bed. EP-A-943595 describes a similar process in which the zeolite adsorbent is zeolite A having, as its exchangeable cations, about 50 to about 85% sodium ions, about 15 to about 40% potassium ions and 0 to 10% of other ions selected from Group IA ions (other than sodium and potassium), Group IB ions, Group IIA ions, Group IIIA ions, Group IIIB ions and lanthanide ions.

In zeolites, it is well-accepted that the control of window size is critically important for achieving high separation selectivities. For a given zeolite structure type, the effective size of the windows can be tuned by partially blocking or unblocking the windows with pre-selected charge-balancing cations. This provides a reasonable but not necessarily optimal control of window size because of the inherent difficulties of precisely placing these cations in a uniform manner throughout the structure. More importantly, the propensity of these cations to promote or participate in undesired chemical transformations that may impart catalytic activity to the material can lead to detrimental oligomerization and polymerization reactions of olefins. These reactions not only lower the recovery of the desired components, they are also likely to render the adsorbent inactive. Both dimethylether and propylene are particularly prone to attack even by mildly acidic sites and this may severely limit the temperature and partial pressures at which the separation processes can be carried out.

In an effort to control chemical reactivity more reliably, there is a growing interest in the use of non-acidic, all-silica, zeolites. Since these siliceous zeolites require no extra-framework balancing cations, the size of the windows is much more uniform throughout the crystals and largely determined by the crystal structure. Thus, for example, the potential of deca-dodecasil 3R (DDR) for separating propane and propylene has been very recently reported. See Zhu, W., Kapteijn, F., and Moulijn, J. A. "Shape Selectivity in the Adsorption of Propane/Propene on the All-Silica DD3R", Chem. Commun. 2453–2454 (1999). This crystalline microporous silicate has a two-dimensional pore system formed by 8-membered rings of tetrahedrally coordinated atoms with a nominal window size of 3.6 Å×4.4 Å (see Atlas of Zeolites Framework Types, Fifth Revised Edition, pages 108–109, 2001). Diffusion and adsorption measurements on this material indicate that only propylene is able to access the interior of the crystallites. The exclusion of propane was suggested as the basis for a very selective separation scheme. The sizes of the deca-dodecasil 3R windows, however, appear to be so close to the effective kinetic diameter of propylene that the diffusion rates are very low and this could lead to undesirably long adsorption and desorption cycles. Cycle duration can, in principle, be reduced by appropriate reductions in crystal size but such changes are not always possible with the known synthetic procedures.

The advantages of reactivity control and size exclusion afforded by materials like DDR may not be sufficient to develop an effective separation process. The window size also has to be optimally controlled such that short duration cycles are achieved. Work by the present inventors has shown that a more optimal control of window size, with a simultaneous control of chemical reactivity, can be obtained with certain crystalline microporous materials containing phosphorous in the framework. For example, aluminophosphate AlPO-34, which is isostructural with chabazite (CHA), has pores defined by a three-dimensional interconnected channel system of 8-membered rings having window sizes of 3.86 Å×4.18 Å. These window sizes were obtained by the Distance-Least-Square method (Ch. Baerlocher, A. Hepp, W. M. Meier, "DLS-76, a program for the simulation of crystal structures by geometric refinement", Lab. f. Kristallographie, ETH, Zürich, 1978), constraining the cell size to that measured for the dehydrated material at 25° C., i.e., rhombohedral cell a, b, c=9.345 Å, and $\alpha$, $\beta$, $\gamma$=94.3°. Since the numbers of Al and P atoms in the unit cell of AlPO-34 are the same, there is no need for balancing cations. The lack of Bronsted acidity in this material not only permits its use as an adsorbent at higher temperatures, it also more properly tailors the size of the windows by changes in the bond angles and bond lengths of the tetrahedrally-coordinated atoms and the bridging oxygens.

The window sizes in these phosphorous-containing materials can be further modified by suitable atomic substitutions that change bond lengths and bond angles while preserving the crystalline structure. Thus, for example, the complete replacement of Al by Ga in the synthesis mixture to give GaPO-34, which is isostructural with AlPO-34, leads to another very effective material for separating propylene and dimethylether from propane. Some of the advantages of AlPO-34 and GaPO-34 can also be found in AlPO-18 (AEI), which has a structure closely related to that of CHA and also comprises a three-dimensional interconnected channel system of 8-membered rings having DLS apertures of 3.61 Å×4.47 Å. Once again, similarly to AlPO-34 and GaPO-34, these dimensions in AlPO-18 represent the actual size of the windows because there is no need for balancing cations.

The diffusivity of a porous crystalline material for a particular sorbate is conveniently measured in terms of its diffusion time constant, $D/r^2$ ($sec^{-1}$), wherein D is the Fickian diffusion coefficient ($cm^2/sec$) and r is radius of the crystallites (cm) characterizing the diffusion distance. In situations where the crystals are not of uniform size and geometry, r represents a mean radius representative of their corresponding distributions. The required diffusion time constants can be derived from standard adsorption uptake kinetics as described, for example, by J. Crank in "The Mathematics of Diffusion", 2nd Ed., Oxford University Press, Great Britain, 1975 or by frequency response methods as described, for example, by Reyes et al. in "Frequency Modulation Methods for Diffusion and Adsorption Measurements in Porous Solids", J. Phys. Chem. B. 101, pages 614–622, 1997.

In accordance with the invention, it has now been found that phosphorus-containing 8-membered ring crystalline microporous molecular sieves, such as AlPO-34 and AlPO-18 and their gallium-containing counterparts, have the capacity of achieving a very effective separation of dimethylether and propylene from propane through a unique combination of diffusion time constants in which the time constants for dimethylether and propylene are not only much higher than propane but they are at the same time also high enough to permit short adsorption/desorption cycles that are economically viable.

U.S. Pat. Nos. 6,293,999 and 6,296,688 disclose the use of AlPO-14 (AFN) for separating propylene from propane. However, although AlPO-14 possesses a set of three-dimensional interconnecting 8-ring channels, only one of them seems large enough to host propylene and therefore AlPO-14 should exhibit a low propylene adsorption capacity. Moreover, with a nominal window size dimension of only 3.3 Å×4.0 Å (Atlas of Zeolites Framework Types, Fifth Revised Edition, pages 36–37, 2001), the diffusion of propylene should be slow and associated with undesirably long adsorption cycles.

SUMMARY

According to the invention there is provided a process for separating propylene and dimethylether from a mixture comprising propylene, dimethylether, and propane comprising the steps of:

(a) passing the mixture through a bed of an adsorbent comprising a porous crystalline material having diffusion time constants for dimethylether and propylene of at least 0.1 $sec^{-1}$, when measured at a temperature of 373° K and partial pressures of dimethylether and propylene of 8 kPa, and having a diffusion time constant for propane, when measured at a temperature of 373° K and a propane partial pressure of 8 kPa, less than 0.02 of said diffusion time constants for dimethylether and propylene; and then (b) desorbing the dimethylether and propylene from the bed.

Preferably, the porous crystalline material is non-acidic.

Preferably, the porous crystalline material is selected from the group consisting of aluminophosphates, gallophosphates, galloaluminophosphates, metalloaluminophosphates and metalloaluminophosphosilicates.

Preferably, the porous crystalline material is selected from the group consisting of AlPO-34, GaPO-34, AlPO-18 and GaPO-18.

Preferably, said mixture is part of an effluent stream from a process for converting oxygenates, such as methanol, to olefins.

DETAILED DESCRIPTION OF THE EMBODIMENTS

Figure 1:
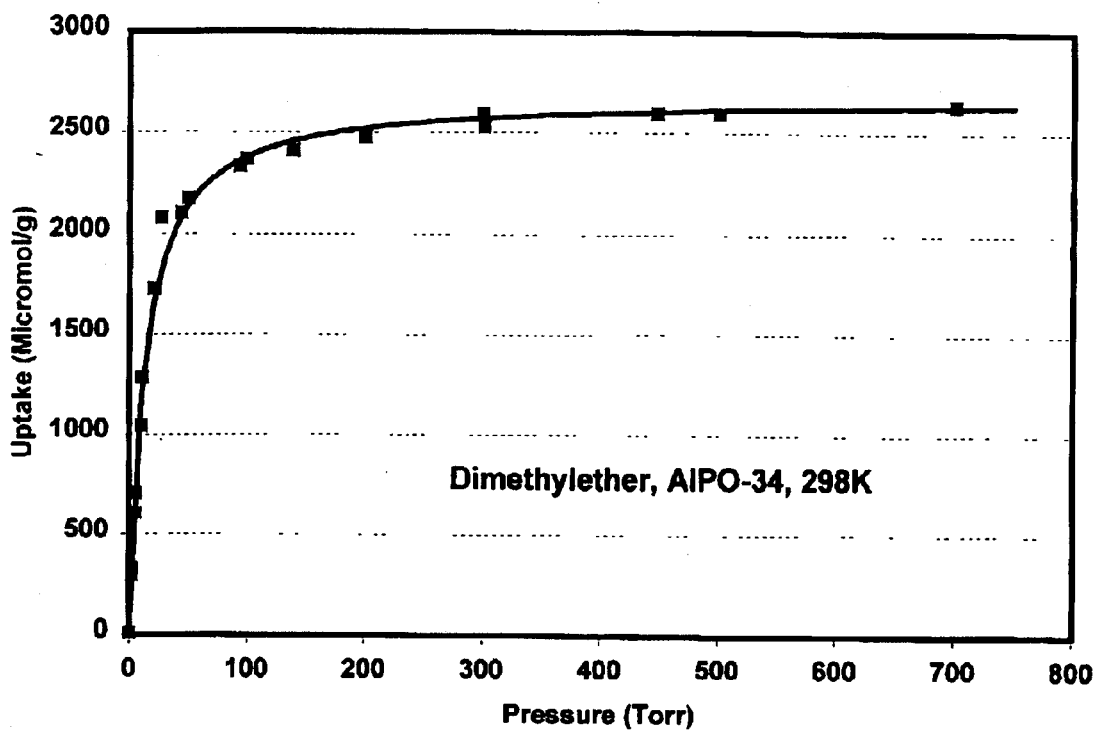
FIGS. 1–4 show adsorption isotherms for dimethylether, propylene, and propane on AlPO-34 at various temperatures.

The present invention provides a process for separating propylene and dimethylether from a mixture comprising propylene, dimethylether, and propane. More particularly, the invention provides a process for converting oxygenates to olefins wherein propylene and dimethylether are separated from an effluent stream of the process which also contains propane. As will be described in detail below, the oxygenate conversion process of the invention involves contacting an oxygenate-containing feedstock, most preferably a methanol-containing feedstock, with a molecular sieve catalyst under conditions to convert the oxygenate-containing feedstock to products composed primarily of light olefins but also containing by-products such as propane and dimethylether.

Molecular Sieves and Molecular Sieve-containing Catalysts

Molecular sieves suited to use in the present invention for converting oxygenates to olefins have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001).

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves of a framework-type selected from the group consisting of AFO, AEL, EUO, HEU, FER, MEL, MFI, MTW, MTT, TON, and substituted forms thereof, and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, which U.S. patents are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 and PCT Publication No. WO 01/62382 (integrated hydrocarbon co-catalyst), PCT WO 01/64340 published Sep. 7, 2001(thorium containing molecular sieve), and R. Szostak, *Handbook of Molecular Sieves*, Van Nostrand Reinhold, New York, N.Y. (1992), which U.S. patents and U.S. application are herein fully incorporated by reference.

The more preferred silicon, aluminum and/or phosphorous containing molecular sieves, and aluminum, phosphorous, and optionally silicon, containing molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

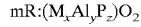

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO11, AlPO-18, AlPO-31, AlPO-34, AlPO-36, AlPO-37, AlPO-46, and metal containing molecular sieves thereof. The more preferred zeolite-type molecular sieves include one or a combination of SAPO-18, SAPO-34, SAPO-35, SAPO-44, SAPO-56, AlPO-18 and AlPO-34, even more preferably one or a combination of SAPO-18, SAPO-34, AlPO-34 and AlPO-18, and metal containing molecular sieves thereof, and most preferably one or a combination of SAPO-34 and AlPO-18, and metal containing molecular sieves thereof.

In an embodiment, the molecular sieve is an intergrowth material having two or more distinct phases of crystalline structures within one molecular sieve composition, in particular, intergrowth molecular sieves are described in U.S. patent application Ser. No. 09/924,016 filed Aug. 7, 2001 and PCT Publ. No. WO 2002070407 published Sep. 12, 2002 and PCT WO 98/15496 published Apr. 16, 1998, which U.S. patent application is herein fully incorporated by reference. In another embodiment, the molecular sieve comprises at least one intergrown phase of AEI and CHA framework-types. For example, SAPO-18, AlPO-18 and RUW-18 have an AEI framework-type, and SAPO-34 has a CHA framework-type.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $AlPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butylamine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is nonionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: $(R-NH)_x$, where $(R-NH)$ is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula:

$(-NHCH_2CH_2-)_m[-N(CH_2CH_2NH_2)CH_2CH_2-]_n$, wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethylenimine, ethoxylated polyethylenimine, polypropylenimine diamine dendrimers (DAB-Am-n), poly(allylamine) [$CH_2CH(CH_2NH_2)$]$_n$, poly(1,2-dihydro-2,2,4-trimethylquinoline), and poly(dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethylenimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil). U.S. Pat. No. 6,503,863 (cooling molecular sieve), U.S. Pat. No. 6,448,197 (metal impregnation including copper), U.S. Pat. No. 6,521,562 (conductive microfilter), and U.S. Pat. No. 6,537,941 (freeze drying the molecular sieve), which U.S. patents are herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), AlPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound AlPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which U.S. patents are herein fully incorporated by reference.

Methods of Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993). In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 $\mu$m to about 300 $\mu$m, preferably from about 50 $\mu$m to about 250 $\mu$m, more preferably from about 50 $\mu$m to about 200 $\mu$m, and most preferably from about 65 $\mu$m to about 90 $\mu$m.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. Pat. No. 6,509,290 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. Pat. No. 6,509,290 (rejuvenation of molecular sieve), which U.S. patents are herein fully incorporated by reference.

Oxygenate Conversion Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, diisopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methylpentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which U.S. patent is herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunji and O. Levenspiel, Robert E. Krieger Publishing Company, New York, N.Y. 1977, which U.S. patents are herein fully incorporated by reference.

The preferred reactor type are riser reactors generally described in *Riser Reactor, Fluidization and Fluid-Particle Systems*, pages 48 to 59, F. A. Zeta and D. F. Othmer, Reinhold Publishing Corporation, New York, 1960, and U.S. Pat. No. 6,166,232 (fast-fluidized bed reactor), U.S. patent application Ser. No. 09/564,613 filed May 4, 2000 and PCT Publication WO01/85872 (multiple riser reactor), which U.S. patent application is herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor (s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. Pat. No. 6,552,240, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is selected from group 13 (IIIA), groups 8, 9 and 10 (VIII) elements) from the Periodic Table of Elements), and a molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000 and PCT Publ. No. 01/94282) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which U.S. patent application is herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001 and PCT Publ. No. WO 2002/068364 which U.S. patent application is herein fully incorporated by reference.

Other methods for operating a regeneration system are disclosed in U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Lauge, *Experimental Techniques, Circulating Fluidized Beds*, Grace, Avidan and Knowlton, eds., Blackie, 1997 (336–337). This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 weight percent coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

A preferred embodiment of a reactor system for the present invention is a circulating fluid bed reactor with continuous regeneration, similar to a modern fluid catalytic cracker. Because the catalyst must be regenerated frequently, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a coke content on regenerated catalyst of no greater than 10 carbon atoms per acid site of the molecular sieve in the catalyst, or the formulated catalyst itself. At least a portion of the regenerated catalyst should be returned to the reactor.

Product Recovery

In the oxygenate conversion process of the invention, particularly where the oxygenate is methanol, the feed is converted to a product composed predominantly of ethylene and propylene (approximately 40 wt % of each component), but also comprising $C_4+$ (approximately 14 wt %), ethane (approximately 1 wt %), propane (approximately 1 wt %) and dimethylether (approximately 1 wt %). This product is then passed to a recovery system for separation of the individual components, particularly the ethylene and propylene.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology, 4th Edition*, Volume 9, John Wiley & Sons, 1996, pages 249–271 and 894–899. Purification systems are also described in for example, U.S. Pat. No. 6,271,428 (purification of a diolefin hydrocarbon stream), U.S. Pat. No. 6,293,999 (separating propylene from propane), U.S. patent application No. 09/689,363 filed Oct. 20, 2000 and PCT Publ. No. WO 02/30857 (purge stream using hydrating catalyst), which U.S. patents and U.S. patent application are herein incorporated by reference.

Typically, a recovery system for use in the process of the invention includes a demethanizer, where the methane is recovered as an overhead stream for use as fuel gas. The bottom fraction from the demethanizer is then fed to a deethanizer, from which the $C_2$-rich overhead stream is passed to a $C_2$-splitter for separation of the ethylene from the ethane. The bottom fraction from the deethanizer is then fed to a depropanizer, from which the $C_3$-rich overhead stream is passed to a $C_3$-splitter for separation of the propylene from the propane and dimethylether, and then to a debutanizer for removal of a $C_4$-rich stream.

In a typical MTO recovery system, the $C_3$-splitter is a multi-stage (N>100) distillation tower designed to give a high level, typically about 98%, recovery of propylene. However, since the propylene recovery in the $C_3$-splitter is always less than 100%, the bottoms stream from the $C_3$-splitter will contain propylene, as well as propane and dimethylether. The process of the present invention seeks to separate the valuable propylene and dimethylether from such a stream.

In the process of the invention, a mixture comprising propylene, dimethylether, and propane is passed through a bed of an adsorbent comprising a porous crystalline material having (i) diffusion time constants for dimethylether and propylene of at least 0.1 $sec^{-1}$, when measured at a temperature of 373° K and dimethylether and propylene partial pressures of 8 kPa, and (ii) a diffusion time constant for propane, when measured at a temperature of 373° K and a propane partial pressure of 8 kPa, less than 0.02 of said diffusion time constants for dimethylether and propylene. Using such a porous crystalline material, the bed preferentially and rapidly adsorbs propylene and dimethylether from the mixture. Thereafter, the propylene and dimethylether can be desorbed from the bed. Thus the process of the invention provides the basis for a very selective kinetic-based pressure or temperature swing adsorption (PSA/TSA) process.

Preferably, the porous crystalline material used in the process of the invention contains framework phosphorus and has at least one system of channels, each defined by an 8-membered ring of tetrahedrally coordinated atoms. More preferably, the porous crystalline material is non-acidic. Suitable porous crystalline materials for use as the adsorbent in the process of the invention include aluminophosphates, gallophosphates, galloaluminophosphates, metalloaluminophosphates and metalloaluminosilicophosphates. Particularly preferred materials include the aluminophosphates AlPO-34 and AlPO-18 and their corresponding gallophosphates GaPO-34 and GaPO-18. AlPO-34 and its synthesis are described in F. Guth, PhD Thesis, Mulhouse Univ., France (1989) or in H. Halvorsen, PhD Thesis, Univ. of Oslo, Norway (1996), whereas AlPO-18 and its synthesis are described in U.S. Pat. Nos. 4,310,440 and 4,385,994, which patents publications are incorporated herein by reference.

Adsorption equilibrium and diffusion studies confirm that AlPO-34 is an excellent material for separating propylene and dimethylether from propane. AlPO-34 is non-reactive, it exhibits a high adsorption capacity, and it rapidly transports propylene and dimethylether while significantly hindering propane. However, while AlPO-34 appears to be an excellent material for separating propylene and dimethylether from propane, there are many other phosphorus-containing crystalline microporous materials that could deliver equal or even improved performance depending on the optimization of the PSA/TSA process. Thus, for example, one can envision process conditions in which lower cycle times may be obtained at the expense of decreased separation selectivity (i.e., lower purity). A material with slightly greater window size could satisfy these conditions. Alternatively, if improvements in separation selectivity justify slightly longer cycle times, it may be advantageous to incorporate selected metals into the framework in such a manner that the effective size of the windows is slightly reduced. In general, the materials needed for specific situations can be optimized by suitable choices of the type of microporous structure, the framework atoms, and the type and charge of any non-framework balancing cations provided that any detrimental chemistry is avoided.

The process of the invention can be carried out in a system comprising a single adsorption bed or a plurality of adsorption beds operated either in phase or out of phase. With a system comprising a single adsorption bed or a plurality of beds operated in phase, the adsorption step must be periodically stopped to permit regeneration of the adsorbent bed(s), whereas when a plurality of adsorption beds are employed in parallel and operated out of phase, one or more beds can be in adsorption service adsorbing the desired gas component, while one or more other units are undergoing regeneration to desorb and collect the adsorbed gas component. Operation of the adsorption process of the invention is cyclical. In the preferred adsorption process, cycles are repeatedly carried out in a manner such that production of the desired product gas is substantially continuous. In the preferred embodiment, therefore, the process is carried out in a system comprising a plurality of adsorption beds arranged in parallel and operated out of phase, such that at least one bed is always in the adsorption phase while another is always in the adsorbent regeneration phase.

The process of the invention may be operated as either a pressure swing adsorption (PSA) process or a temperature swing adsorption (TSA) process. In either case, the precise steps used in carrying out the separation are not critical to the invention.

In general, the basic steps in a PSA process include an adsorption vessel pressurization step, a production (adsorption) step and an adsorbent regeneration step. During the vessel pressurization step, the pressure in the adsorption vessel in which the adsorption process is carried out is raised to the desired adsorption pressure. During the production step, a gaseous propylene, dimethylether, and propane-containing feed is passed through the adsorption vessel at the desired adsorption pressure. As the feed gas passes through the adsorption vessel, a propylene- and dimethylether-enriched component is adsorbed and a propylene- and dimethylether-depleted non-adsorbed gas fraction passes out of the adsorption vessel. The bed regeneration step is carried out by reducing the pressure in the adsorption vessel so as to desorb the propylene- and dimethylether-enriched product gas from the vessel.

The temperature at which the adsorption step of the PSA process is carried out is not critical but in general will be between about 273° K and about 523° K, or more preferably between about 293° K and about 473° K. The upper temperature is selected so as to achieve a significant loading onto the material and to avoid the possibility of any unwanted reactions, such as oligomerization and/or polymerization of the propylene. The pressures at which the adsorption and adsorbent regeneration steps are carried out are likewise a matter of choice, and in general, these steps can be carried out at any of the usual pressures employed for gas PSA processes. The pressure at which the adsorption step is carried out is determined by economics. Typically, the adsorption step is carried out at propylene partial pressures in the range of about 3 kPa to about 300 kPa, and preferably in the range of about 5 kPa to about 200 kPa. Typically, the adsorbent regeneration step is carried out at pressures in the range of about 0.1 kPa to about 10 kPa, and preferably in the range of about 0.2 kPa to about 5 kPa.

Where the process of the invention is operated as a TSA process, the production (adsorption) step is carried out at one temperature and an adsorbent regeneration step is carried out at another higher temperature so as to desorb the propylene- and dimethylether-enriched component adsorbed during the production step. In this case, the adsorption step is carried out at temperatures in the range of about 273° K to about 473° K, preferably in the range of about 293° K to about 423° K, while the adsorbent regeneration step is carried out at temperatures in the range of about 373° K to about 573° K, preferably in the range of about 423° K to about 523° K. The adsorption and regeneration steps in a TSA process are typically carried out at dimethylether and propylene partial pressures in the range of about 10 kPa to about 300 kPa, and preferably in the range of about 20 kPa to about 200 kPa.

After removal of the propane, the propylene and dimethylether produced by the separation process of the invention are conveniently recycled back to the oxygenate conversion step so that the dimethylether can be converted to additional olefin product.

The invention will now be more particularly described with reference to the following Examples and the accompanying drawings.

EXAMPLE 1

Figure 2:
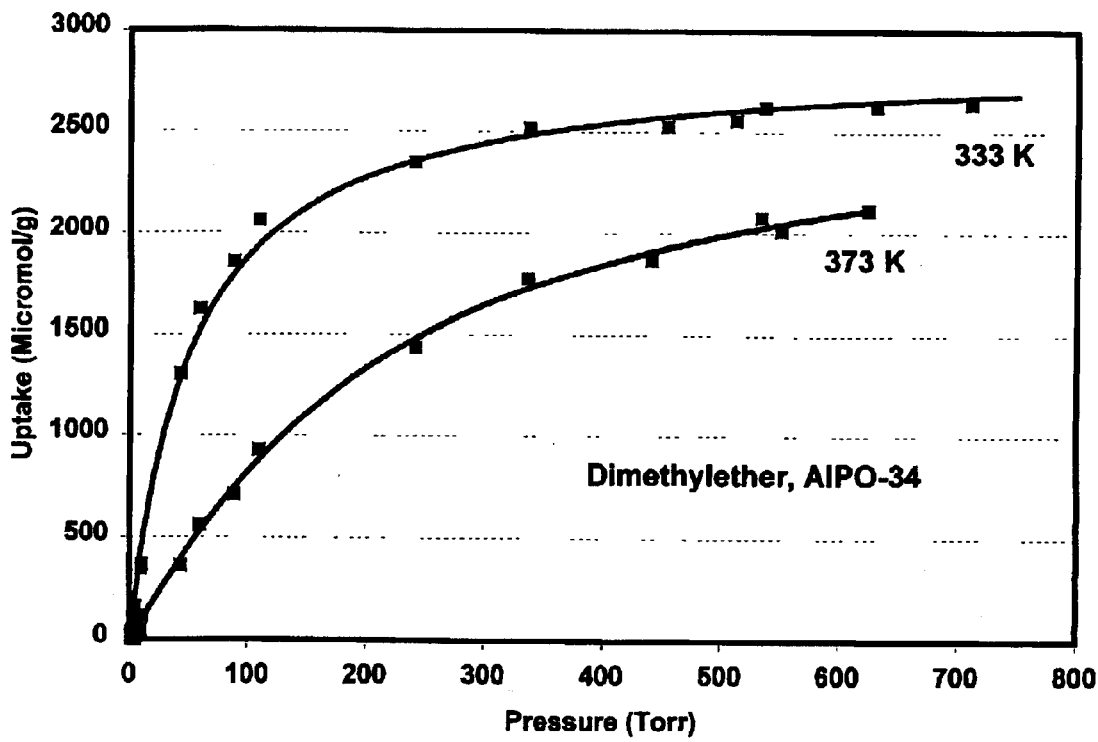
Figure 3:
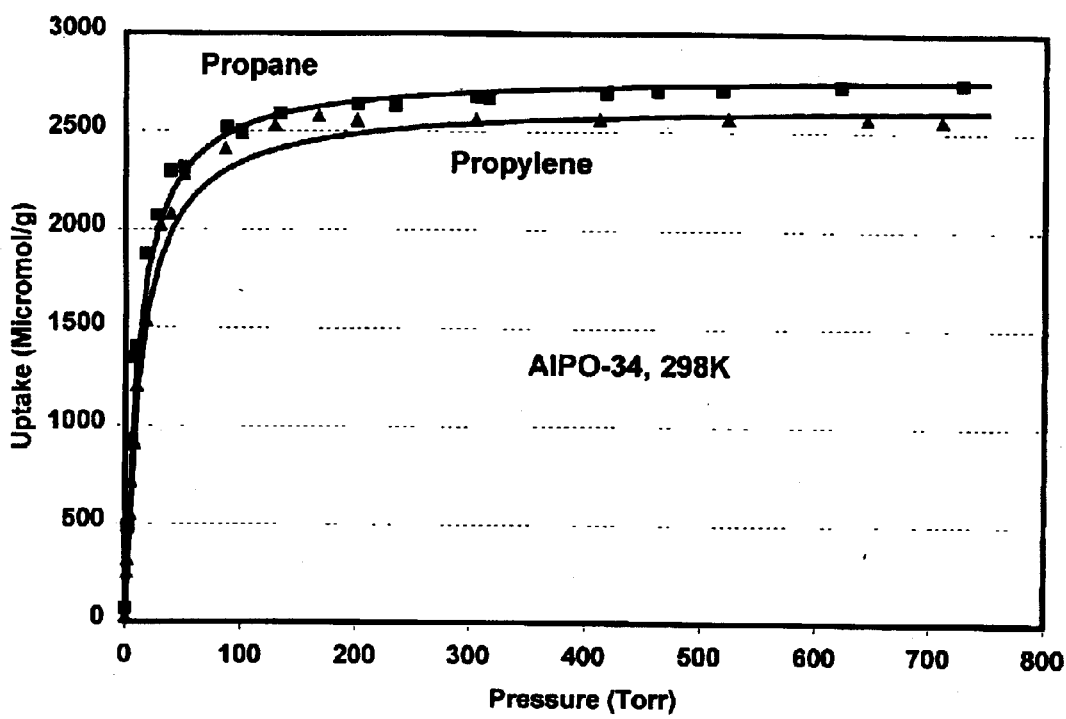
Figure 4:
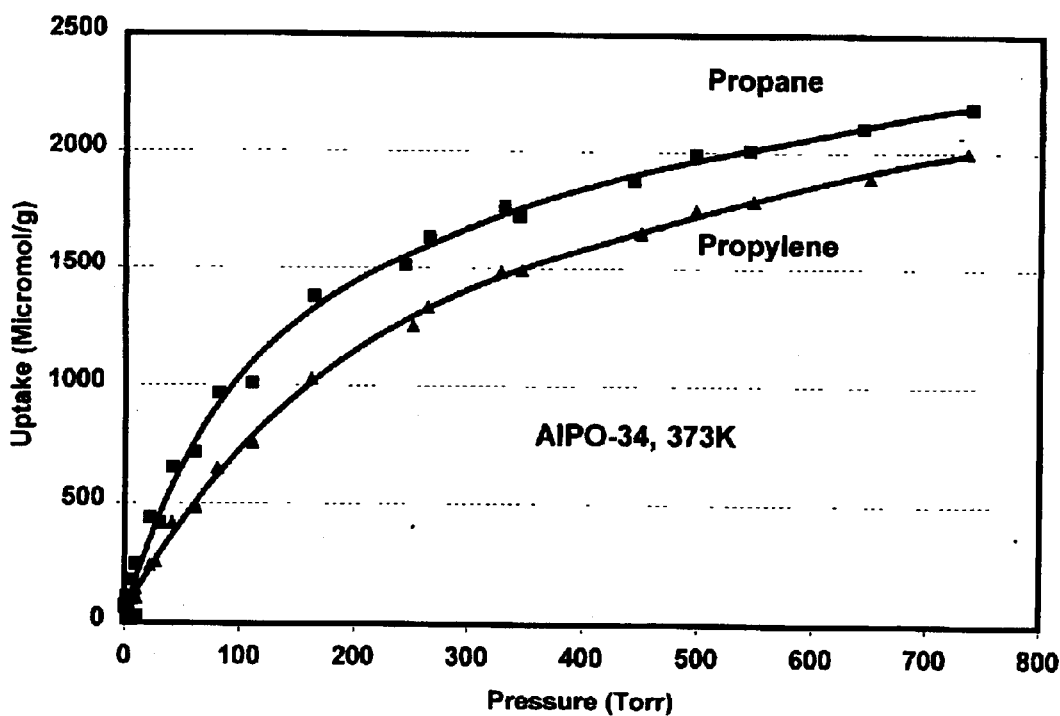

Studies were conducted on the equilibrium uptakes of dimethylether, propylene, and propane on AlPO-34 at various temperatures. FIGS. 1 and 2 show the adsorption isotherms for dimethylether on AlPO-34 at 298° K, 333° K, and 373° K. FIGS. 3 and 4 show the adsorption isotherms for propylene and propane on AlPO-34 at 298° K and 373° K. These figures show that the total uptakes remain high even at relatively high temperatures. The similarity of the adsorption isotherms for dimethylether, propane, and propylene on AlPO-34 strongly suggests that any separation selectivity achieved with these materials is primarily the result of window size and molecular diameter effects instead of specific energetic interactions with the adsorbent. The high adsorption capacity for propane is not a concern because the low diffusion rates limit its access to the interior of the crystals during the duration of the adsorption cycle.

EXAMPLE 2

Figure 5:
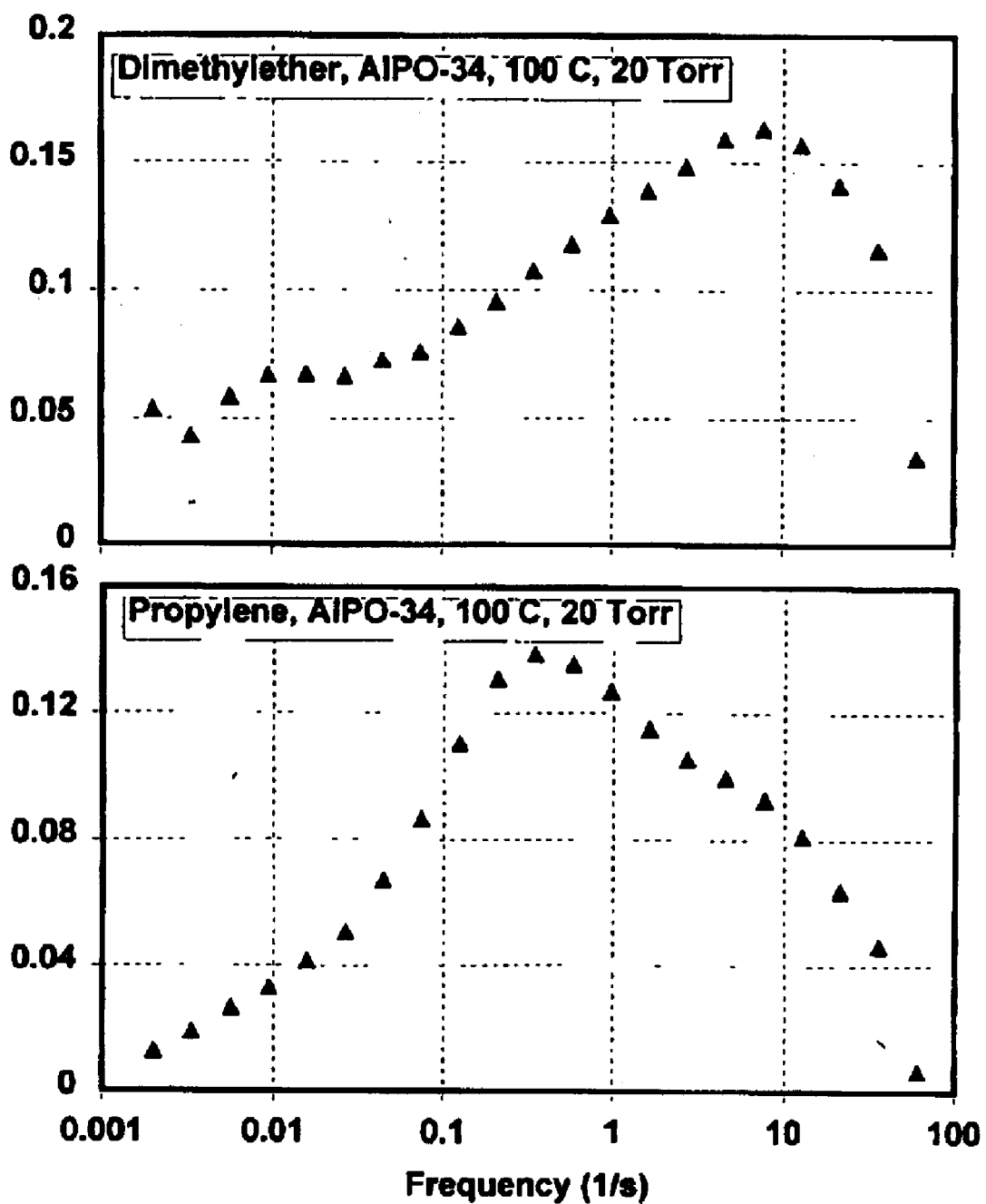
FIGS. 5–7 show frequency response measurements on AlPO-34 for dimethylether, propylene, and propane at 2.66 kPa (20 Torr) and various temperatures.
Figure 6:
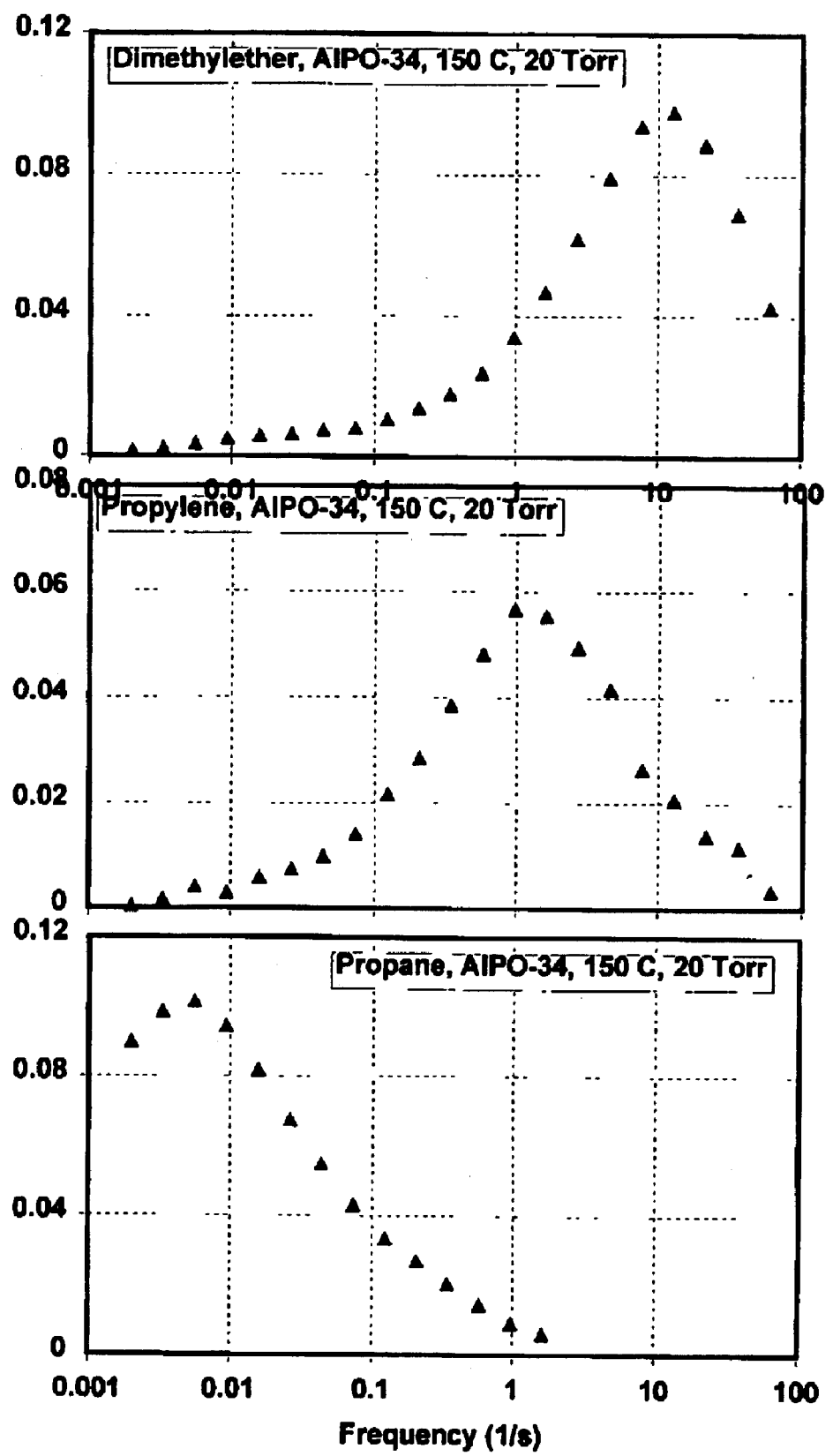
Figure 7:
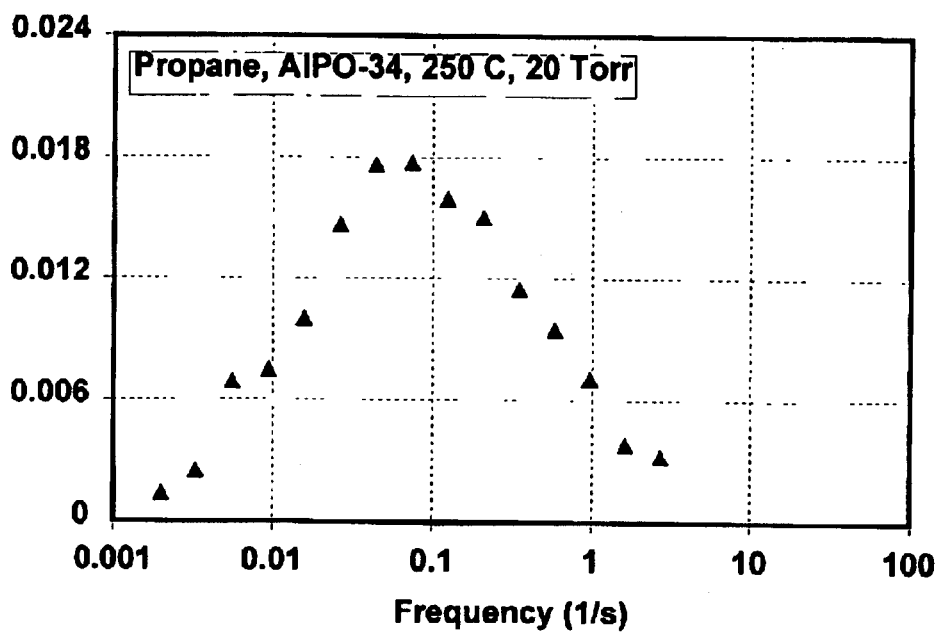

A dynamic technique, frequency response, was employed to measure the diffusion time constants of dimethylether, propane, and propylene on AlPO-34. FIG. 5 summarizes some typical frequency response experiments for dimethylether and propylene on AlPO-34 at 2.66 kPa (20 Torr) and a temperature of 373° K. The frequency (i.e., abscissa) at which the data goes through a maximum directly gives the diffusion time constant for the corresponding system (see for example: Reyes et al. in "Frequency Modulation Methods for Diffusion and Adsorption Measurements in Porous Solids", J. Phys. Chem. B. 101, pages 614–622, 1997). FIG. 5 shows that the diffusion time constants for dimethylether and propylene are greater than 0.1 $sec^{-1}$. At this temperature of 373° K, the diffusion time constant for dimethylether is more than an order of magnitude greater than for propylene, while that for propane is very small and below the lower detection limit (~0.002 $sec^{-1}$) of the frequency response instrument. By raising the temperature to 423° K, while keeping the pressure at 2.66 kPa, FIG. 6 shows that the diffusion time constant for propane approaches 0.01 $sec^{-1}$, while the diffusion time constants for dimethylether and propylene exceed 1 and 10 $sec^1$, respectively. This figure then clearly shows that dimethylether and propylene diffuse more than 100 and 1000 times faster than propane, respectively, at the particular conditions of the experiment. As expected from the temperature dependence of the diffusion process, propane undergoes the most change for a change in temperature. Consistent with expectations, the changes in diffusion time constants for dimethylether and propylene are less pronounced, and the corresponding difference between them also becomes less, as temperature increases. The change in diffusion time constant with temperature for propane is further illustrated in FIG. 7. This figure shows that at 523° K the diffusion time constant for propane, which reaches a value of about 0.1 sec$^{-1}$, is still much lower than the diffusion time constants for either dimethylether or propylene at a temperature that is 100° K lower (i.e., 423° K). The results of FIGS. 5–7 clearly demonstrate that dimethylether and propylene can be very effectively separated from propane via a kinetic-based PSA or TSA scheme.

EXAMPLE 3

Figure 8:
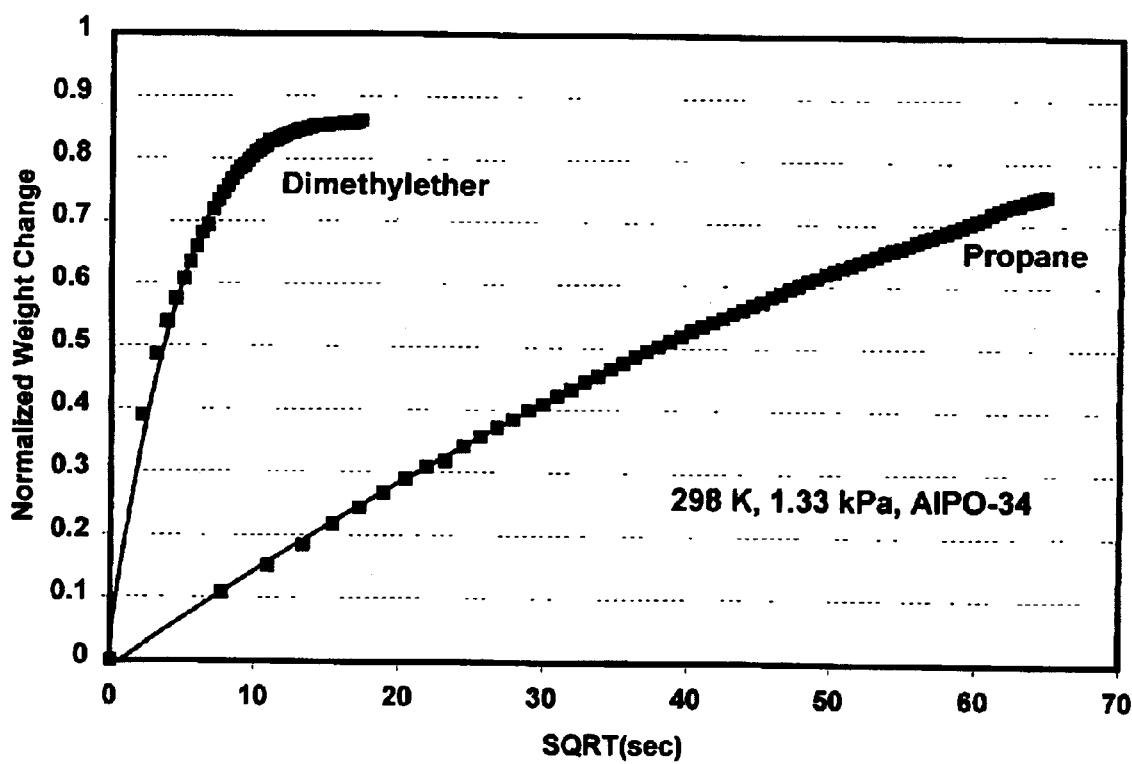
FIG. 8 shows adsorption uptake kinetics for dimethylether and propane on AlPO-34 at 298° K and 1.33 kPa (10 Torr).

Adsorption uptake kinetics for dimethylether and propane on AlPO-34 were carried out at 298° K and 1.33 kPa. FIG. 8 displays the normalized weight change versus the square root of time ("SQRT(sec)"). The slope at early times is proportional to the square root of the diffusion time constant (see for example J. Crank in "The Mathematics of Diffusion", 2nd Ed., Oxford University Press, Great Britain, 1975). FIG. 8 clearly confirms that the diffusion time constant for dimethylether is much greater than for propane. The time taken for dimethylether to adsorb to a significant extent provides guidance on the duration of the adsorption step that is required for an effective separation scheme. The choice of this time ultimately impacts purity and recovery.

What is claimed is:

1. A process for separating propylene and dimethylether from a mixture comprising propylene, dimethylether, and propane comprising the steps of:
   (a) passing the mixture through a bed of an adsorbent comprising a porous crystalline material having diffusion time constants for dimethylether and propylene of at least 0.1 sec$^{-1}$ when measured at a temperature of 373° K and dimethylether and propylene partial pressures of 8 kPa and having a diffusion time constant for propane measured at a temperature of 373° K and a propane partial pressure of 8 kPa less than 0.02 of said diffusion time constants for dimethylether and propylene; and then
   (b) desorbing the dimethylether and propylene from the bed.

2. The process of claim 1, wherein the porous crystalline material contains framework phosphorus and has at least one system of channels, each defined by an 8-membered ring of tetrahedrally coordinated atoms.

3. The process of claim 1, wherein the porous crystalline material is non-acidic.

4. The process of claim 1, wherein the porous crystalline material is selected from the group consisting of aluminophosphates, gallophosphates, galloaluminophosphates, metalloaluminophosphates, and metalloaluminophosphosilicates.

5. The process of claim 1, wherein the porous crystalline material is selected from the group consisting of AlPO-34, AlPO-18, GaPO-34 and GaPO-18.

6. The process of claim 1, wherein the porous crystalline material is AlPO-34.

7. The process of claim 1, wherein the porous crystalline material is AlPO-18.

8. The process of claim 1, wherein the porous crystalline material is GaPO-34.

9. The process of claim 1, wherein the porous crystalline material is GaPO-18.

10. The process of claim 1, wherein the process is a pressure swing adsorption process and step (a) is effected at dimethylether and propylene partial pressures in the range of about 3 kPa to about 300 kPa and step (b) is effected at dimethylether and propylene partial pressures in the range of about 0.1 kPa to about 10 kPa.

11. The process of claim 10, wherein step (a) is effected at dimethylether and propylene partial pressures in the range of about 5 kPa to about 200 kPa and step (b) is effected at dimethylether and propylene partial pressures in the range of about 0.2 kPa to about 5 kPa.

12. The process of claim 10, wherein step (a) is effected at a temperature in the range of about 273° K to about 523° K.

13. The process of claim 1, wherein the process is a temperature swing adsorption process and step (a) is effected at a temperature in the range of about 273° K to about 473° K and step (b) is effected at a temperature in the range of about 373° K to about 573° K.

14. The process of claim 13, wherein step (a) is effected at a temperature in the range of about 293° K to about 423° K and step (b) is effected at a temperature in the range of about 423° K to about 523° K.

15. The process of claim 13, wherein step (a) is effected at dimethylether and propylene partial pressures in the range of about 3 kPa to about 300 kPa.

16. The process of claim 1, wherein said mixture comprising propylene, dimethylether, and propane is part of an effluent stream from a process for converting oxygenates to olefins.

* * * * *